United States Patent [19]

Bogan

[11] Patent Number: 4,738,663
[45] Date of Patent: Apr. 19, 1988

[54] HYPODERMIC NEEDLE SHIELD

[76] Inventor: David B. Bogan, 15587 N. Bank Rd., Roseburg, Oreg. 97470

[21] Appl. No.: 58,190

[22] Filed: Jun. 4, 1987

[51] Int. Cl.⁴ .............................................. A61M 5/32
[52] U.S. Cl. ..................................... 604/198; 604/263
[58] Field of Search ................ 604/198, 197, 192, 263

[56] References Cited

U.S. PATENT DOCUMENTS

| | | | |
|---|---|---|---|
| 2,925,083 | 2/1960 | Craig | 604/197 |
| 3,487,834 | 1/1970 | Smith, Jr. et al. | 604/197 X |
| 4,655,751 | 4/1987 | Harbaugh | 604/198 |

Primary Examiner—John D. Yasko
Attorney, Agent, or Firm—Chernoff, Vilhauer, McClung & Stenzel

[57] ABSTRACT

The syringe shield of the present invention is comprised of a sleeve guide having a pair of fasteners with cavities formed in them that fit over the flange which are located on hypodermic syringes for grasping by the user's fingers. The fastener pieces snap together to lock the syringe guide on the syringe flange and index it so that it does not cover the volumetric indicia which is located on the syringe. The sleeve guide has elongate fingers which extend along the sides of the syringe and act as a track which a transparent tubular sleeve travels on. The sleeve has slots which overlie the sleeve guide fingers, and moves between an extended position, where it covers the needle attached to the syringe, and a retracted position, where it does not cover the needle. Detents associated with the syringe guide fingers lock the sleeve in its retracted and extended positions, although the detent which locks the sleeve in its retracted position can easily be overcome merely by pushing the sleeve towards the needle.

11 Claims, 1 Drawing Sheet

U.S. Patent   Apr. 19, 1988   4,738,663
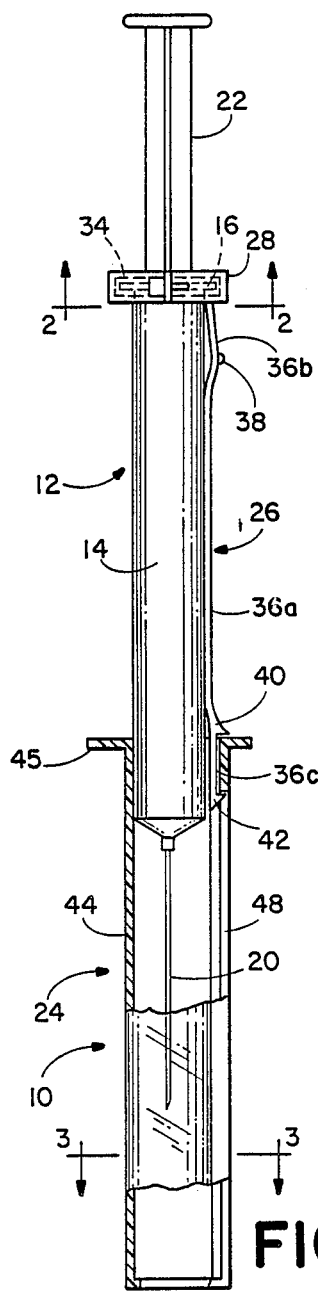
FIG.1
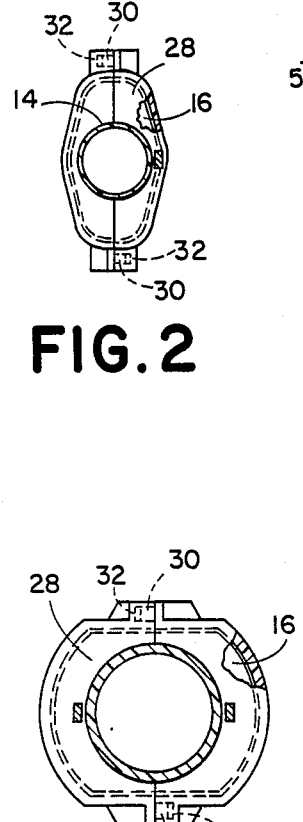
FIG.2
FIG.5
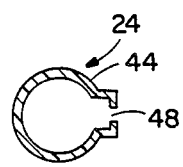
FIG.3
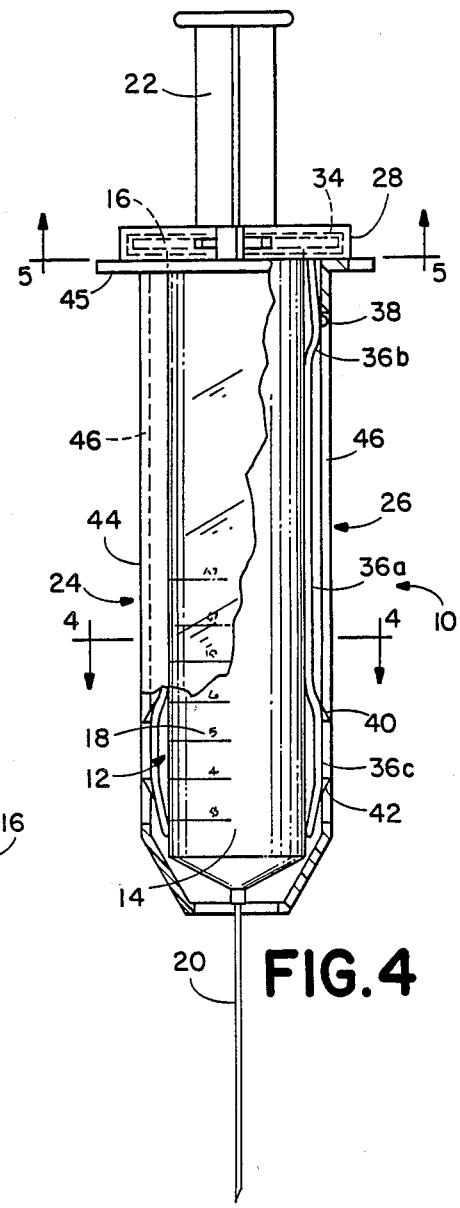
FIG.4
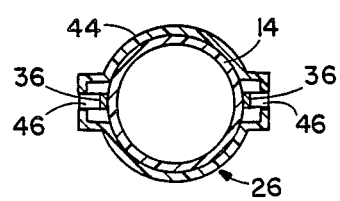
FIG.6

HYPODERMIC NEEDLE SHIELD

BACKGROUND OF THE INVENTION

This invention relates to a needle shield for a hypodermic syringe and needle assembly, and in particular to such a shield which can be activated simply by the application of a linear pushing force in a direction away from the point of the needle.

Covering the needle of a hypodermic syringe after it has been used is extremely important since accidental sticking by a contaminated needle is a frequent source of disease transmission. The traditional cover which is placed over a hypodermic needle by its very nature leads to needle stick since it must be moved toward the needle and if the user does not succeed in placing the cover over the needle the fingers holding the cover probably will be stuck. Such a cover also is susceptible of becoming misplaced. Finally, the installation of such a cover requires a concentrated effort making it a common practice to delay installation of the cover until after an emergency situation has abated thereby creating the possibility of accidental needle stick in the interim.

Accordingly, attempts have been made to provide a needle shield which is attached to the syringe before its use and which can be placed in a position around the needle without the necessity of moving the hands toward the needle. However, the prior art devices of this type all have disadvantages which have prevented their widespread acceptance.

One shortcoming of the prior art shields is that they are complex or utilize a complex latching system. Thus, they are expensive to manufacture, are cumbersome to use and are difficult to latch and unlatch. A prior art device which typifies this problem is La Marche, U.S. Pat. No. 1,921,034.

While somewhat less expensive to manufacture, and simpler to use than La Marche, devices such as those shown in Mitchell, U.S. Pat. No. 4,631,057 and Sampson et al., U.S. Pat. No. 4,573,976 have inherent installation problems. First, they either press fit or are glued onto the syringe they are used with and thus must be sized to fit a particular syringe body exactly. Accordingly, a shield must be made for each different syringe on the market. In addition, if it is not oriented correctly when it is installed, the shieldlatching mechanism of Sampson et al., '976, will cover the volumetric indicia located on the syringe.

Sampson et al., U.S. Pat. No. 4,425,120 provides a much simpler device but it again has installation and operational shortcomings. The pins 47, which carry the shield, must either be manufactured as an integral part of the syringe or they must be installed later by adhesive. The former makes installation of the shield on existing syringes impossible, and the latter is labor intensive and prone to breakage. Furthermore, the Samson et al. '120 cover creates the indexing difficulties mentioned above. In addition, the necessity to rotate the device to unlock and again lock it requires concentration of the user which, in an emergency situation, will result in a delay in deploying the shield. Finally, a locking mechanism of this type can easily become dislodged thereby allowing the shield to fall back away from its extended position.

The present invention overcomes the foregoing shortcomings and limitations of the prior art syringe shields by providing a sleeve guide which attaches to the flange of a hypodermic syringe and a shield which travels on the sleeve guide between extended and retracted positions. The sleeve guide has a two-piece fastener which snaps together over the syringe flange. Thus, the device is easily installed without the necessity that the sleeve guide create a press fit with the chamber of the syringe or be glued to it. Since the size and shape of syringe flanges are fairly uniform, and the fastener does not have to fit the flange precisely, only a few sleeve guides are required to accommodate most existing syringes. Furthermore, since syringe flanges are elongate, in order to accommodate the fingers of the users, the sleeve guide can only be installed in a particular rotational position relative to the chamber of the syringe and thus will not inadvertently cover the volumetric indicia on the syringe.

Depending on the size of the syringe, the sleeve guide has one or two fingers which extend along the sides of the syringe. The fingers have center portions which contact the sides of the chamber of the syringe and inner and distal portions which bow out from the chamber. The fingers are made from a flexible material so that the inner and distal portions can be deflected to where they also are substantially flush with the chamber.

The sleeve which fits over the sleeve guide is a cylindrical tube having a diameter which allows it to fit loosely over the center portions of the fingers but not fit over the inner and distal portions without their being deflected. The sleeve has one or two slots, depending on whether the sleeve guide it will be used with has one or two fingers, and the slots extend across substantially all of its longitudinal extent. The ends of the sleeve guide are open and the end facing the syringe has an annular ledge protruding from its periphery. The sleeve is transparent in order to permit reading the volumetric indicia located on the chamber of the syringe.

As the sleeve is inserted onto the sleeve guide, the distal portions of the fingers are deflected until they reach the slots in the sleeve and then they protrude through the slots to provide tracks for the sleeve to travel along without rotating. When the sleeve is fully inserted on the sleeve guide the needle extends out of it and is uncovered. When in this retracted position the inner portions of the fingers are located inwardly of the slots and thus are deflected by the sleeve. Protrusions located on the inner portions of the fingers are positioned where they will project into the slots and contact their bottom edges. Thus, the protrusions prevent the sleeve from inadvertently being moved from its retracted position.

After the syringe and needle assembly has been used, the ledge at the bottom of the sleeve is pushed which causes the sleeve to pass over the protrusions. The sleeve then is slid along the fingers to an extended position where it completely covers the needle. Since the user contacts the sleeve at the end opposite the needle, and the sleeve is being pushed away from the point of the needle, the user's fingers will not be stuck by the needle while performing this operation. In the extended position the distal portions of the fingers are located beneath the portion of the sleeve which extends below the slots and thus are deflected by the sleeve. A pair of prongs is located on each distal portion such that when the sleeve is in its extended position one of the prongs extends into the slot and engages its bottom edge to prevent the shield from being pulled off of the sleeve guide, and the other prong fits behind the shield to prevent it from being slid back to its retracted position. Thus the needle cannot inadvertently be exposed and the assembly can be discarded in normal trash receptacles.

Since it is easy to move the shield to its extended position, and since there is no danger of being stuck by the needle when doing so, the user normally will move the shield to its extended position immediately after the syringe and hypodermic assembly is used.

Accordingly, it is a principal object of the present invention to provide a needle shield for a hypodermic syringe and needle assembly which can be attached easily to existing syringes.

It is a further object of the present invention to provide such a needle shield which is universal and will fit on most pre-existing syringes.

It is a further object of the present invention to provide such a needle shield which attaches to the syringe through a snap-together fastener.

It is a still further object of the present invention to provide such a needle shield where the snap-together fastener is self-aligning so that the needle shield never obscures the volumetric indicia located on the syringe.

It is a yet further object of the present invention to provide such a needle shield wherein movement to an extended position, where it covers the needle, is along a linear path.

It is a further object of the present invention to provide such a needle shield which is moved to its extended position merely by being pushed in a direction away from the point of the needle.

It is a still further object of the present invention to provide such a needle shield which does not interfere with the operation of the syringe.

The foregoing and other objectives, features and advantages of the present invention will be more readily understood upon consideration of the following detailed description of the invention taken in conjunction with the accompanying drawings.

BRIEF DESCRIPTION OF THE DRAWINGS

FIG. 1 is a side view, partially broken away to show hidden detail, of a hypodermic syringe and needle assembly having a first embodiment of the needle shield of the subject invention installed on it.

FIG. 2 is a sectional view taken along the line 2—2 in FIG. 1.

FIG. 3 is a sectional view taken along the line 3—3 in FIG. 1.

FIG. 4 is a second embodiment of the needle shield of the present invention installed on a syringe.

FIG. 5 is a sectional view taken along the line 5—5 of FIG. 1.

FIG. 6 is a sectional view taken along the line 6—6 of FIG. 1.

DETAILED DESCRIPTION OF A PREFERRED EMBODIMENT

Referring to FIGS. 1 and 4 of the drawings, the needle shield 10 of the present invention is used with a disposable hypodermic syringe and needle assembly 12 of the type which is in widespread use in the health care industry. The syringe has a cylindrical chamber 14 with a flange 16 located at one end which is arranged to be supported by the fingers of a user. The flange is wider in one direction than it is in the other direction. In the smaller style syringe illustrated in FIGS. 1 and 2, which typically is used for home injections of insulin, the flange comprises back-to-back truncated triangles. In the larger style syringe illustrated in FIGS. 4 and 5, the flange is rectangular with rounded ends. The chamber 14 has numbers 18 printed on one side which are used to determine the volume of fluid in the chamber.

The end of the chamber opposite the end having the flange 16 is fluidly interconnected with an elongate hollow needle 20 having a sharpened point. The end of the chamber having the flange 16 is open and has a plunger 22 located in it which is used to draw fluid into the chamber and then dispense it through the needle.

The needle shield comprises two sections, a sleeve 24 and a sleeve guide 26. The sleeve guide is attached to the syringe by means of a snap-together fastener 28. The fastener is in two pieces which have protruding pins on one side of their adjoining surfaces and holes 32, which receive the pins in a press fit, on the other side. Thus, the two sides can be placed around the chamber 14 of the syringe and snapped together to make an integral unit. The fastener has a cavity 34 which fits around the flange 16 when the two pieces are snapped together. Since the flange is not completely symmetrical, the fastener can only be installed on the syringe in 90° opposed radial orientations, thereby making the sleeve guide self-indexing, as will be more fully explained later.

In the embodiment illustrated in FIGS. 4, 5 and 6, each piece of the fastener has an elongate finger 36 extending from it which is positioned along the side of the chamber 14. In the embodiment illustrated in FIGS. 1, 2, and 3, only one piece of the fastener contains a finger 36. In both embodiments the fingers contain medial portions 36a which contact the sides of the chambers and inner portions 36b, and distal portions 36c which bow out from the chamber. The fingers 36 are made from a flexible plastic, however, so that their inner and distal portions will be deflected inwardly toward the chamber when pressure is applied to them. Located medially on the inner portions 36b of the fingers are outwardly projecting, semi-cylindrical protrusions 38. Located at the lower ends of the distal portions are outwardly projecting first prongs 40, and located at the upper ends of the distal portions are outwardly protruding second prongs 42.

The sleeve 24 is a cylindrical tube 44 having an inner diameter which is slightly greater than the outer diameter of the chamber 12 and a length which is approximately equal to the length of the chamber. Both ends of the sleeve are open and it has an annular ledge 45 at the end which faces the syringe. The sleeve is transparent in order that the user can read the numbers 18 located on the chamber.

In the embodiment illustrated in FIGS. 4, 5 and 6, the sleeve has two slots 46, one on each side, and in the embodiment illustrated in FIGS. 1, 2, and 3, the sleeve has one slot 48. The slots 46 and 48 are straight and have the same width as the fingers 36. The slots extend over substantially, but not all, of the length of the sleeve. At the end of the sleeve which faces the syringe, the slots terminate immediately beyond the protrusions 38 when the sleeve is fully retracted onto the syringe, FIG. 4. Thus, the protrusions 38 extend into the slots when the sleeve is in its fully retracted position and prevent the sleeve from moving out of this position. However, since the inner portions of the finger, on which the protrusions 38 rest, are deflectable, the sleeve can be moved out of its retracted position merely by pushing on the ledge 45. The other ends of the slots terminate outwardly of the distal portions 36c when the sleeve is in its retracted position. Thus, the distal portions extend through the slots to act as tracks along which the sleeve can be slid between its retracted position and an extended position where the sleeve covers the needle, FIG. 1.

The fingers are oriented on the fasteners 28 such that the sole finger is 180° opposed from the numbers 18 in the embodiment illustrated in FIGS. 1, 2, and 3 and the two fingers are 90° opposed from the numbers 18 in the embodiment illustrated in FIGS. 4, 5 and 6. Since the sleeve travels along the fingers without rotating, the slots remain rotationally opposed to the numbers at all times also and therefore do not interfere with the reading of the numbers.

The first and second prongs 40 and 42 are separated from one another by a distance which is equal to the distance between the bottoms of the slots 46 or 48 and the bottom of the sleeve. As a result when the sleeve is in its fully extended position the first prongs engage the bottom of the syringe to prevent the sleeve from sliding back to its retracted position, and the second prongs engage the bottoms of the slots to prevent the sleeve from being pulled off of the syringe. If desired a cap (not shown) can be inserted into the opening at the end of the sleeve to further isolate the needle.

In use, the sleeve guide 26 is installed on a syringe by placing the two fastener pieces 28 around the syringe flange 16 and locking them together by urging the pins 30 into the mating holes 32. The sleeve 24 then is inserted onto the sleeve guide by aligning the slots 46 or 48 with the fingers 36. As the sleeve is inserted onto the sleeve guide the distal portions 36c are deflected until the slot reaches them. The sleeve can then be kept in the extended position shown in FIG. 1 or it can be moved to the retracted position shown in FIG. 4 and the needle covered by a traditional cap (not shown) until the syringe and needle assembly is ready to be used. If the sleeve is kept in the extended position it must be moved to the retracted position prior to use.

When the sleeve is in its retracted position the protrusions 38 engage the bottoms of the slots 46 or 48 and prevent the sleeve from moving to its extended position. However, after the syringe and needle assembly has been used, the sleeve can be moved to its extended position, where it encloses the needle and prevents accidental needle stick of a person who is handling the assembly, merely by pushing on the ledge 45. Pushing the sleeve causes the inner portions 36b of the fingers to be deflected so that the sleeve is freed of the protrusions 38. The distal portions 36c of the fingers then act as tracks along which the sleeve is moved to its extended position. As the sleeve reaches its extended position it contacts the first prongs 40 which causes the distal portions of the fingers to be deflected. After the bottom portion of the sleeve passes over the first prongs, the distal portions 36c expand somewhat to lock the bottom portion of the sleeve between the first prongs 40 and the second prongs 42, thereby keeping the sleeve in its extended position where it covers the needle 20.

Since the sleeve is moved to its extended position by pushing it in a direction away from the point of the needle, there is no chance of the user being stuck by the needle while performing this operation. Once the sleeve is in its extended position it cannot accidentally be deflected to expose the needle. As a result the syringe and needle assembly no longer pose a threat and can be disposed of without the necessity of special handling.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A needle shield for a hypodermic syringe and needle assembly of the type having a cylindrical chamber with a protruding flange located at one end, an elongate hollow needle protruding from the other end and a plunger which enters the chamber at the end containing the flange and is movable therein for ejecting liquids contained in the chamber out of the needle, said shield comprising:
   (a) a sleeve guide having at least one elongate finger;
   (b) a snap-together fastener which attaches said sleeve guide immovably to said flange with said elongate finger being disposed along the side of said chamber;
   (c) a sleeve which fits over said sleeve guide and which has a track defined therein which engages said finger and which allows said sleeve to be slidably moved along said finger between an extended position where it completely encloses said needle and a retracted position where said needle is substantially exposed.

2. The needle shield of claim 1 wherein said chamber has volumetric indicia inscribed thereon and said sleeve is made from a transparent material which permits reading said indicia therethrough and said snaptogether fastener includes means for rotationally indexing said sleeve guide relative to said syringe automatically when said fastener is installed on said flange in a manner such that said finger and track do not cover said indicia.

3. The needle shield of claim 1 wherein said finger includes means for inserting said sleeve over said sleeve guide when it is attached to said flange.

4. The needle shield of claim 3 wherein said finger includes detent means for releasably indexing said sleeve at its extended and retracted positions.

5. The needle shield of claim 3 wherein said finger includes stop means for preventing said sleeve from being removed from said sleeve guide.

6. The needle shield of claim 5 wherein said finger engages said track in a manner which prevents said sleeve from rotating relative to said sleeve guide as it is moved between its extended and retracted positions.

7. The needle shield of claim 6 wherein said finger and said track both are straight and are aligned with the longitudinal axis of said cylinder.

8. The needle shield of claim 5 wherein said track comprises an elongate slot and said finger includes an inner portion, which is located proximate said fastener and projects through said slot when positioned beneath it, a medial portion which does not project through said slot when positioned beneath it and a distal portion which projects through said slot when positioned beneath it, said inner and distal portions being deflectable so as to fit within said sleeve when not positioned beneath said slot.

9. The needle shield of claim 8 wherein said slot extends over less than the entire longitudinal extent of said finger and said detent means comprises a protrusion located on said inner portion of said finger which engages the margin of said slot which is towards said flange when said sleeve is in its extended position.

10. The sleeve guide of claim 8 wherein said detent further comprises a first prong, located on said distal portion, which engages the end of said sleeve when said sleeve is in its extended position.

11. The sleeve guide of claim 9 wherein said stop means comprises a second prong, located on said distal portion, which engages the margin of said slot which is towards said needle when said needle is in its extended position.

* * * * *